United States Patent [19]
Gmeiner et al.

[11] Patent Number: 5,457,187
[45] Date of Patent: Oct. 10, 1995

[54] OLIGONUCLEOTIDES CONTAINING 5-FLUOROURACIL

[75] Inventors: William H. Gmeiner; Patrick L. Iversen, both of Omaha, Nebr.

[73] Assignee: Board of Regents University of Nebraska, Lincoln, Nebr.

[21] Appl. No.: 164,089

[22] Filed: Dec. 8, 1993

[51] Int. Cl.$^6$ .......................... C07H 21/02; C07H 21/04
[52] U.S. Cl. ............................... 536/25.5; 514/50
[58] Field of Search ............................... 536/25.5; 514/50

[56] References Cited

U.S. PATENT DOCUMENTS

| | | | |
|---|---|---|---|
| 3,905,953 | 9/1975 | Kotick et al. | 536/25.4 |
| 4,701,521 | 10/1987 | Ryser et al. | 530/322 |

OTHER PUBLICATIONS

Tanaka et al. Cancer Research 41: 4132–4135, 1981.
Venkataraman et al. Biochim. Biophys. Acta 741: 224–229.
Marasco, et al., *A Convenient Method for the Direct Incorporation of 5–Fluoro–2'–deoxycytidine into Oligodeoxynucleotides*, J. of Org. Chem., vol. 57, 1992.
Miwa, et al., *Comparative Studies on the Antitumor and Immunosuppressive Effects of the New Fluorouracil Derivative $N^4$–Trimethoxybenzoyl–5'–deoxy–5–fluorocytidine and Its Parent Drug 5'–Deoxy–5–fluorouridine*, Chem. Pharm. Bull., vol. 38, No. 4, pp. 998–1003, 1990.
Ouchi, et al., *Synthesis and Antitumor Activity of Conjugates of 5–fluorouracil and chito–oligosaccharides Involving a Hexamethylene Spacer Group and Carbamoyl Bonds*, Drug, Design and Delivery, vol. 6, pp. 281–187, 1990.
Schmidt, et al., *Chemical Synthesis of 2'–deoxyoligonucleotides Containing 5–fluoro–2'–deoxycytidine*, Nucleic Acids Research, vol. 20, No. 10, pp. 2421–2426, 1992.

*Primary Examiner*—Douglas W. Robinson
*Assistant Examiner*—Gary L. Kunz
*Attorney, Agent, or Firm*—Henderson & Sturm

[57] ABSTRACT

A homo-oligonucleotide of between 2 and 26 monomers of 5-fluorouridine 5'-monophosphate or 5-fluorodeoxyuridine 5'-monophosphate covalently linked via 3'- to 5'-phosphodiester linkages, where at the 3'- or 5'- terminus there is covalently linked a molecule selected from the group consisting of cholesterol, ethyl-spaced adamatane, 1,2-di-hexadecylglycerol and poly-L-lysine. These homo-oligonucleotides exhibit antitumor activity.

12 Claims, 7 Drawing Sheets

Oligomeric 5-fluorouridine X=OH
Oligomeric 5-fluorodeoxyuridine X=H

OLIGONUCLEOTIDES CONTAINING 5-FLUOROURACIL

CROSS REFERENCES RELATED APPLICATIONS

The present application is an original patent application and is currently not known to be related to any co-owned and co-pending application.

GOVERNMENT RIGHTS

The present invention was privately funded. The federal government has no rights in the present invention.

TECHNICAL FIELD

The present invention is generally related to chemotherapeutic treatments and more specifically to methods for increasing the in-vivo half-life and target specificity of chemotherapeutic drugs such as 5-fluorouracil.

BACKGROUND ART

Anti-metabolite nucleosides and nucleoside analogues have found widespread use in the treatment of cancer and other human diseases. 6mercaptopurine was found by Elion and co-workers to interfere with purine metabolism and is used in the treatment of leukemia. Other nucleosides or nucleosides analogues that are of use include trifluorothymidine, arabinosyl cytidine.

5-Fluorouracil (5-FU) has been used continuously since its development in 1957 by Duusinski and Heidelberger (U.S. Pat. No. 2,802,005) for the treatment of solid tumors of the head, neck, breast, and colon. 5-FU was originally designed to work as an inhibitor of thymidylate synthetase (TS). TS is the enzyme which converts deoxyuridine 5'-O-monophosphate (dUMP) to deoxythymidine 5'-O-monophosphate (dTMP). It is believed that 5-FU retards tumor expansion by causing thymidine pools to become depleted in rapidly proliferating tumor cells.

Protocols for the administration of 5-FU for treatment of human cancer involve infusion of the drug for long periods of time. 5-FU is rapidly metabolized and excreted with a half-life in-vivo of about 18 minutes. While 5-FU is an effective anti-cancer agent when metabolically activated to become an inhibitor of TS its effectiveness is hampered by rapid metabolism and formation of 2-fluoro-$\beta$-alanine (FBAL) which is neurotoxic and cardiotoxic. For these reasons researchers and clinicians have long desired a method of increasing the therapeutic index and target specificity), of 5-FU.

A variety of pro-drug forms of 5-FU have been developed to address the issues of cellular uptake, sustained release, organ distribution, and transdermal or intestinal uptake that are problematic for the native drug. One of the most widely studied pro-drug forms of 5-FU is 5'-deoxy-5-fluorouridine (DFUR). DFUR is converted to 5-FU by pyrimidine nucleoside phosphorylase but has better cellular uptake properties than 5-FU. Like 5-FU, DFUR also releases FBAL as a toxic metabolite. Other nucleoside analogues of FUr include Tegafur [(1-(2-tetrahydrofuryl)-5-fluorouracil], Ftorafur [R,S-1-(tetrahydro-2-furanyl)- 5-fluorouracil] and a variety of 5-fluorocytidine derivatives.

A variety of polymeric forms of 5-fluorouridine have also been prepared to provide sustained release of 5-FU. 5-Fluorouracil has been prepared as a conjugate of chito-oligosaccharides and also as a conjugate of poly(ethylene glycol). These polymeric forms were designed to provide macromolecular drugs with reduced side-effects and strong anti-tumor activity and showed good biological activity and low toxicity in animal models. The chief advantages of $FdU_n$ and $FrU_n$ compared to other polymeric structures are that the oligonucleotide based oligomers are readily taken up by cells, perhaps through a facilitated mechanism. Also, enzymatic degradation of the oligomeric 5-fluorodeoxyuridine results directly in release of the fully activated inhibitor of thymidylate synthase (FdUMP). Oligonucleotide based polymers retain the advantages that make other polymers useful such as increased bioavailability. Homo-oligomeric compositions of other nucleoside antimetabolites benefit from positive increase in bioavailability and cellular uptake. Homo-oligomeric anti-metabolite nucleotides are synthesized and used as a polymeric drug delivery system.

DISCLOSURE OF INVENTION

Homo-oligomeric 5-fluorouridine and 5-fluorodeoxyuridine ($FrU_n$ and $FdU_n$, n=oligomer length) are synthesized and used as a polymeric drug delivery system for production of FdUMP, the potent inhibitor of thymidylate synthetase (TS) and an important target in cancer chemotherapy. Disclosed are methods of both preparing and utilizing these novel compositions. The oligomeric compounds of the present invention efficiently transverse the cellular membranes of a variety of cell lines and are degraded to an active form (FdUMP in the case of $FdU_n$). $FdU_n$ is a more effective cytotoxic agent in cell culture on a per residue basis than is monomeric 5-fluorodeoxyuridine. Based on data from other oligonucleotide drugs these oligomeric compounds have a significantly longer in-vivo residence time compared with monomeric compounds. The advantages of a longer residence time in-vivo, and greater cytotoxicity per residue of 5-fluorodeoxyuridine, demonstrates that oligomeric 5-fluorodeoxyuridine is therapeutically useful at lower doses than are monomeric 5-fluorouridine, 5-fluorodeoxyuridine, and 5-fluorouracil. Thus, delivery of FdUMP as $FdU_n$ is more cost effective on a per dose basis and less neurotoxic and cardiotoxic than delivery in a monomeric form. The reduced neuro- and cardiotoxicity is a consequence of lower levels of 2-fluoro-$\beta$-alanine (FBAL) released from the lower effective dosage. $FdU_n$ and $FrU_n$ are representative of a class of homo-oligomeric anti-metabolite compounds that include homo-oligomeric 6-mercaptopurine, homo-oligomeric araC, and homo-oligomeric 5-trifluoromethyl thymidine and other homo-oligomers of bioactive nucleosides and nucleoside analogues. In all cases the oligomeric form allows increased bio-availability and improved cellular uptake.

Delivery of $FrU_n$ results in degradation by nuclease to FUMP. FUMP is acted upon by kinases to form FUTP. FUTP is incorporated into cellular RNA. Normal turnover at cellular RNA releases FUMP which may be converted by a series of enzymatic steps to form FdUMP. Delivery of $FrU_n$ thus results in sustained production of FdUMP that may be important in inhibiting DNA replication in slowly dividing cells. The compounds of the present invention also have an added advantage in being homopolymers in synthesis. In a range of lengths (e.g. 8 to 12), acceptable for administration as a chemotherapeutic agent, such oligomers may be synthesized in solution (and the proper length species separated). This method is much more cost-effective than solid-phase synthesis and HPLC purification which are necessary in antisense oligonucleotides. Thus the present invention discloses a method of delivering anti-cancer and anti-viral nucleosides in oligomeric form to overcome the rapid metabolism and excretion of monomeric nucleosides, nucleoside bases, and nucleoside analogues.

OBJECTS OF THE INVENTION

Delivery of these nucleosides as homo-oligomeric nucleotides confers several distinct advantages relative to their delivery as nucleoside bases, nucleosides, or analogues:

The polymeric form increases bioavailability relative to the monomeric forms. The increased bioavailability results in a more convenient administration schedule than available for the monomeric forms.

The oligonucleotide compounds are actively taken up by cells resulting in a higher intracellular concentration from the oligonucleotide based drug than for the monomeric forms. This results in a greater proportion of drug inside tumor cells.

Enzymatic degradation of these homo-oligomeric nucleotides by 3'-exonucleases releases the nucleoside 5'-O-monophosphate. Thus, the NMPs are the fully metabolically activated product, e.g. FdUMP, is readily converted to the fully activated metabolic product, e.g., araCTP. Several steps of metabolic activation may be bypassed and nonproductive pathways of metabolic activation are avoided.

The before mentioned advantages significantly reduce the dose required for a positive biological response and reduce dose-dependent toxic side-effects. Therefore, these homo-oligomeric nucleotides provide higher therapeutic indices while additionally being more cost-effective than their monomeric counterparts.

MODES FOR CARRYING OUT THE INVENTION

I. Introduction

The delivery of nucleosides and nucleoside analogues that have anti-cancer and anti-vital activity as monomers in the form of homo-oligomeric nucleotides (oligonucleotides composed of a single type of nucleotide, e.g., dA) has significant advantages relative to their delivery as monomers.

It should be apparent to individuals skilled in the art that equivalence substitutions for 5-FU may be made, for example (1) pyrimidine analogues such as CYTARABINE™"ara-C", azauridine, azaribine, 5-chlorodeoxyuridine, 5-bromodeoxyuridine, 5-iododeoxyuridine, 5-trifioromethyldeoxyuridine; and (2) purine analogues such as 6-thioguanine, 6-mercaptapurine, azathioprine, "2'deoxycofermycin" PENTOSTATIN™, erythrohydroxynonyladenine.

These agents are or have been employed as anti-cancer immunosuppressant therapeutics. Since they generally have short half-lives and their utility is limited by the toxicity of their metabolites they may all show significant advantages as homo-oligomeric polymers relative to their monomeric congeners.

For example, homo-oligomeric nucleotides, (due to their higher molecular weight), have increased bioavailability relative to their constituent mononucleosides (which are readily metabolized and excreted). Homo-oligomeric nucleotides may also be taken up via a receptor and more efficiently gain entry to the cell than mononucleotides. Once taken up by cells, such compounds are readily degraded by exonucleases to their 5'-O-monophosphate form (frequently the bio-active form of the nucleoside).

Figure 1:
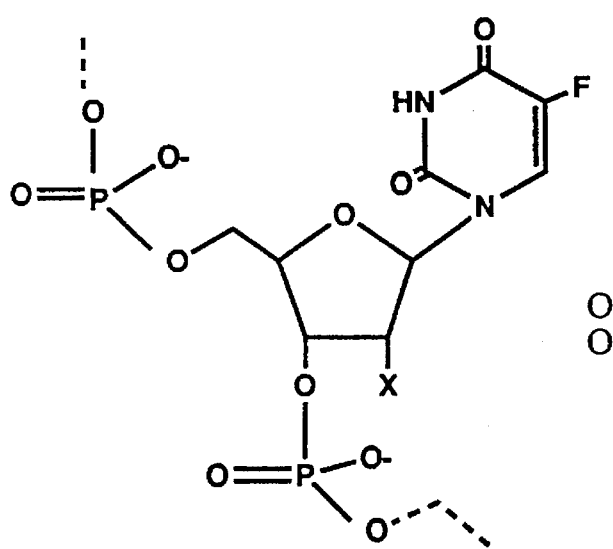
FIG. 1 is a diagram illustrating the chemical structure of a monomer of oligomeric 5-fluorouridine-5'-O-monophosphate.
Figure 2:
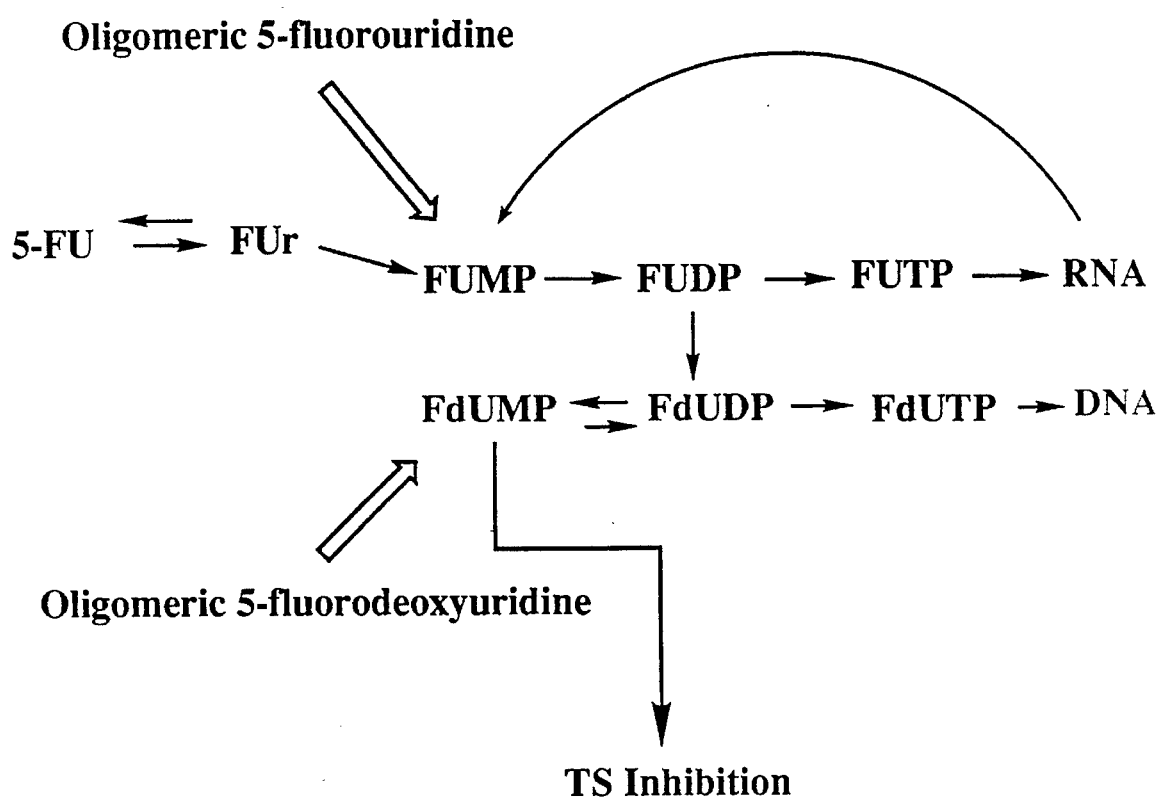
FIG. 2 is a diagrammatic illustration of the metabolic pathway of 5-FU and the entry points for the products of exonuclease action on $FdU_n$ and $FrU_n$.

The present invention describes a method of utilizing oligomeric forms of 5-FU (e.g., $FdU_n FrU_n$ [FIG. 1]) for anti-cancer treatments. 5-Fluorouracil (5-FU) is used frequently in the treatment of solid tumors of the gastrointestinal tract, breast, ovary, and skin. In an effort to increase clinical effectiveness, numerous studies have been conducted to better understand the mechanisms by which 5-FU is cytotoxic. Despite the enormity of these efforts the objective response rates for 5-FU chemotherapy, either singularly or in combination with other drugs, range from 10 to 33%, with cures being achieved rarely.

The present invention teaches novel compositions and methods of: (1) delivering 5-FU and related compounds in order to maximize intracellular concentration of the metabolite(s) responsible for 5-FU cancer cell cytotoxicity; (2) overcoming 5-FU's relatively poor bioavailability and the toxicity of its metabolites (chiefly the neurotoxicity of FBAL); and (3) enhancing the delivery of cytotoxic metabolite(s) such that (a) the cytotoxic metabolite delivery is timed for optimum tumor cell destruction, (b) the cytoxic metabolites are tumor target specific, and (c) tumor cell uptake is optimized.

II. Synthesis of $FdU_n$ and $FrU_n$ Species

All synthetic reactions are performed under an inert atmosphere in oven-dried glassware and followed by thin layer chromatography in appropriate solvent systems. Intermediates are preferably analyzed by 300 MHz 1H NMR spectroscopy and critical intermediates and final products are preferably characterized by 1H, 13C NMR spectroscopy and mass spectrometry. Solvents and starting reagents may be purchased from Aldrich Chemical Company. Radioactive substances may be purchased from Dupont New England Nuclear.

Those skilled in the art of biochemical synthesis may produce $FdU_n$ and $FrU_n$ and their conjugates, according to the present invention, wherein the following syntheses are currently preferred. Other homo-oligomeric nucleotides may be prepared in completely analogous fashion.

5'-O-[4,4'-dimethoxytrityl]-5-fluorouridine 5.244 gins. (20 mMoles) of 5-fluorouridine is dissolved in 20 mL anhydrous pyridine and then dried under vacuum.

This procedure is repeated at least one more time in order to make 5-fluorouridine devoid of moisture. The dried 5-fluorouridine is then dissolved in 20 mL of pyridine. 8.131 gms (24 mMoles, 1.2 eq.) of 4,4'-dimethoxy trityl chloride is added as solid in 4 fractions over a period of 2 hours. The reaction mixture is then stirred at room temperature overnight and is then diluted with 25 mL of dichloromethane and washed with saturated sodium bicarbonate solution. The aqueous layer is then washed with 20mL dichloromethane. The organic layers are mixed and washed with saturated bicarbonate solution two more times. The organic layer is then dried over anhydrous sodium sulphate. The solvent is removed under vacuum to yield a yellow foam which is purified on a silica gel column using 90:10 chloroform::methanol as eluent. The 4, 4'-dimethoxytrityl derivative of 5-fluorodeoxyuridine is prepared in an analogous manner.

Rf=0.523 in chloroform:methanol(90:10)

MS, m/z 303.1 (DMtrityl cation), 587.1 (M+Na$^+$), 609.1 (M+2Na$^+$)

5'-O-[4,4'-dimethoxytrityl]-[2'-O-t-butyl-dimethylsilyl]-5-fluorouridine 10 gms(18 mMoles) of 5'-O-[4,4'-dimethoxytrityl]-5-fluorouridine is dried from pyridine under vacuum to make it free of moisture and then dissolved in 40mL pyridine and 4.95 imidazole g (72 mMoles, 4 eq) is added. The solution is stirred for an hour and then 3 gms (20 mMoles, 1.1 eq) tert-butyl dimethyl silyl chloride is added as solid in a single portion. The reaction is allowed to proceed for 5 hours at room temperature. A similar work up with aqueous saturated sodium bicarbonate is followed. The crude product is purified on a silica gel column using 65:35 hexane:ethyl acetate as eluent. The bis-silyl and two monosilyl products are separated and the correct monosilyl isomer is used for phosphorylation reaction.

Rf=0.457 (bis silyl product) 0.286 (2'-silyl isomer) 0.114 (3'-silyl isomer)in 65:35 hexane:ethyl acetate MS, m/z 303.2 (Dmtrityl cation), 815.5 (M+Na$^+$) - bis silyl product m/z 303.0 (DMtrityl cation), 701.0 (M+Na$^+$) - 2'-silyl isomer m/z 303.0 (DMtrityl cation), 701.0 (M+Na$^+$) - 3'-silyl isomer 5'-O-[4,4'-dimethoxytrityl]-[3'-O-diisopropylcyanoethyl phosphonamidic-chloride]-[2'-O-t-butyl-dimethylsilyl]-5-fluorouridine To a stirred THF solution of 1.5 mL(11.6 mMoles, 4 eq.) diisopropylethylamine, 88 mg. (0.73 mMoles, 0.25 eq.) DMAP, and 1.03 mL(4.35 mMoles, 1.5 eq. ) of 2-cyanoethyl-N,N-diisopropylchlorophosphoramidite are added, dropwise, a solution of 2 g (2.9 mMoles) of 2'-monosilyl trityl 5-FU in equal volume of THF at room temperature with stirring. After stirring for 4 hours the reaction mixture is worked up by diluting with 20 mL ethyl acetate and washed five times with saturated sodium chloride solution. The solvent is removed under vacuum and the residue is purified on a silica gel column using 90:10 chloroform:triethylamine as eluent. The product obtained is a white foam. The phosphoramidite of the 5'-O-[4-4"-dimethyloxytrityl]-5-fluorodeoxyuridine is prepared in a like manner.

Rf=0.45 in 90:10 chloroform:triethylamine

MS, m/z 303.1 (trityl cation), 901.3 (M+Na$^+$)

A. Synthesis of [4-$^{14}$C] 5-fluorouridine

Figure 5:
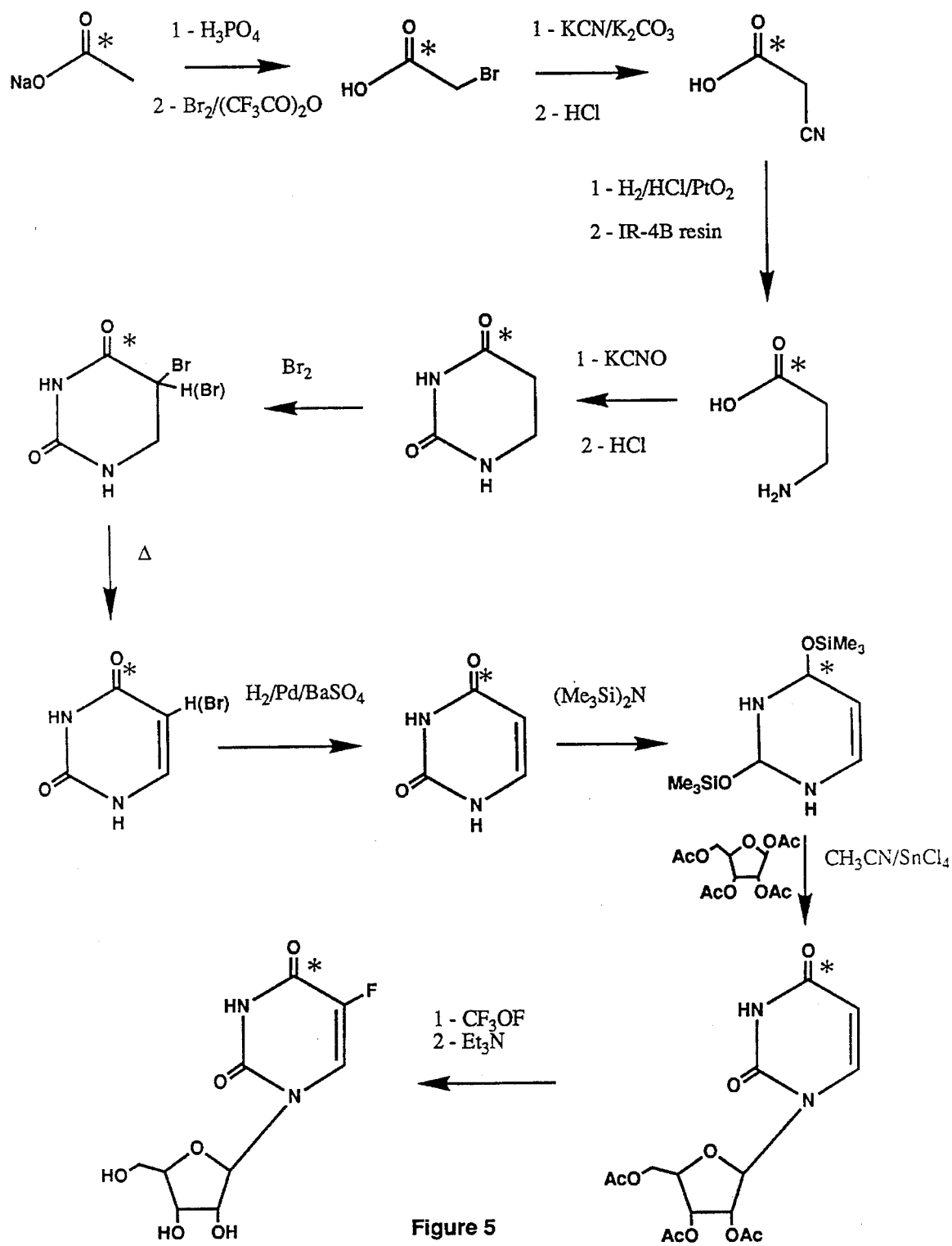
FIG. 5 is a diagrammatic illustration showing a preferred method of preparing [4-$^{14}$C]5-fluorouridine for incorporation into oligomers.

The following methodology may be useful to those practicing the invention wherein radio-labelled forms of the oligomers of the present invention are desired. The synthesis of [4-$^{14}$C] 5-fluorouridine is shown in FIG. 5. The $^{14}$C isotope is preferred over the more readily obtained $^3$H isotope since it is not exchanged in acidic subcellular compartments or tissues. Although [2-$^{14}$C] 5-fluorouridine is known in the art, the [4-$^{14}$C] compound is not. Introduction of $^4$C at the 4 position is preferred following metabolism since it is retained in FBAL (a neurotoxic catabolite of 5-fluorouridine). The $^{14}$C probe allows straightforward analysis of metabolism by radio-detected HPLC. The synthetic procedure for preparation of [4-$^{14}$C]-5-fluorouridine (FIG. 5) is based on the synthesis of 2', 3', 5'-tri-O-benzoyl [4-$^3$C] uridine (Roberts & Poulter). The original source of $^{14}$C for this synthesis is 1-$^{14}$C sodium acetate. The acetate is brominated at the 2 position and the bromine is then displaced by cyanide. The cyano group is then reduced over a platinum catalyst and the terminal amine reacted with the isothiocyanate to form the dihydropyrimidine. The 5,6 double bond is introduced by dehydrobromination to form uracil. Glycosylation is accomplished by treating the O-acetyl sugar with a Lewis acid in acetonitrile after protecting the uracil carbonyls as the O-trimethylsilyl derivatives. Fluorination at the desired position is then induced by the Robins method (treatment with trifluoromethyl fluoride). Formation of the deoxynucleoside is accomplished by selective reduction of the 2'-OH using tri-butyl tin hydride after protection of the 3' and 5' hydroxyls with di-isopropyl disiloxane in anhydrous THF. The 5'-O-4,4'-dimethoxytrityl derivatives of [4-$^{14}$C]5-fluorouridine and [4-$^{14}$C]-5-fluorodeoxyuridine are prepared by treating the nucleosides with 4,4'-dimethoxytrityl chloride in pyridine. The 2'-O-t-butyl-dimethyl-silyl derivative of the ribonucleoside is prepared by treatment with t-butyl-dimethyl-silyl-chloride in dry THF and is separated from the 3'-isomer and the bis-silylated product by preparative normal phase HPLC. Reactive phosphoramidites are prepared by reaction with cyanoethylphosphonamidic-chloride using Hunigs base in dry THF and purified by column chromatography on silica gel.

B. Synthesis and Purification of FdU$_n$ and FrU$_n$

The controlled pore glass support used for solid phase synthesis of FdU$_n$ is prepared by reacting the 5'-O-[4,4'-dimethoxytrityl]-5-fluorodeoxyuridine first with succinic anhydride to form the 3'-O-succinate and then with long-chain alkylamine controlled pore glass in the presence of catalytic amounts of dimethylaminopyridine and stochiometric amounts of 1-(3-dimethylaminopropyl)-ethylcarbodiimide in anhydrous pyridine. The controlled pore glass support used for solid phase synthesis of FrU$_n$ is prepared by reacting 5'-O-[4,4'-dimethoxytrityl]-[2'-O-t-butyl-dimethylsilyl]-5-fluorouridine in an analogous manner. The loading capacity for both FdU$_n$ and FrU$_n$ derivatized CPG is determined by trityl analysis at 600 nm following exposure to acid. The derivatized support is then suspended in a mixture of acetic anhydride (5 mL), 2,4,6 collidine (7 mL), and DMAP (3 g) in anhydrous THF (100 mL) and shaken for two hours. The CPG is then washed with dichloromethane and loaded at the appropriate capacity, e.g., 1 or 10 µmole, into columns for use in an ABI solid-phase DNA synthesizer.

Figure 3:
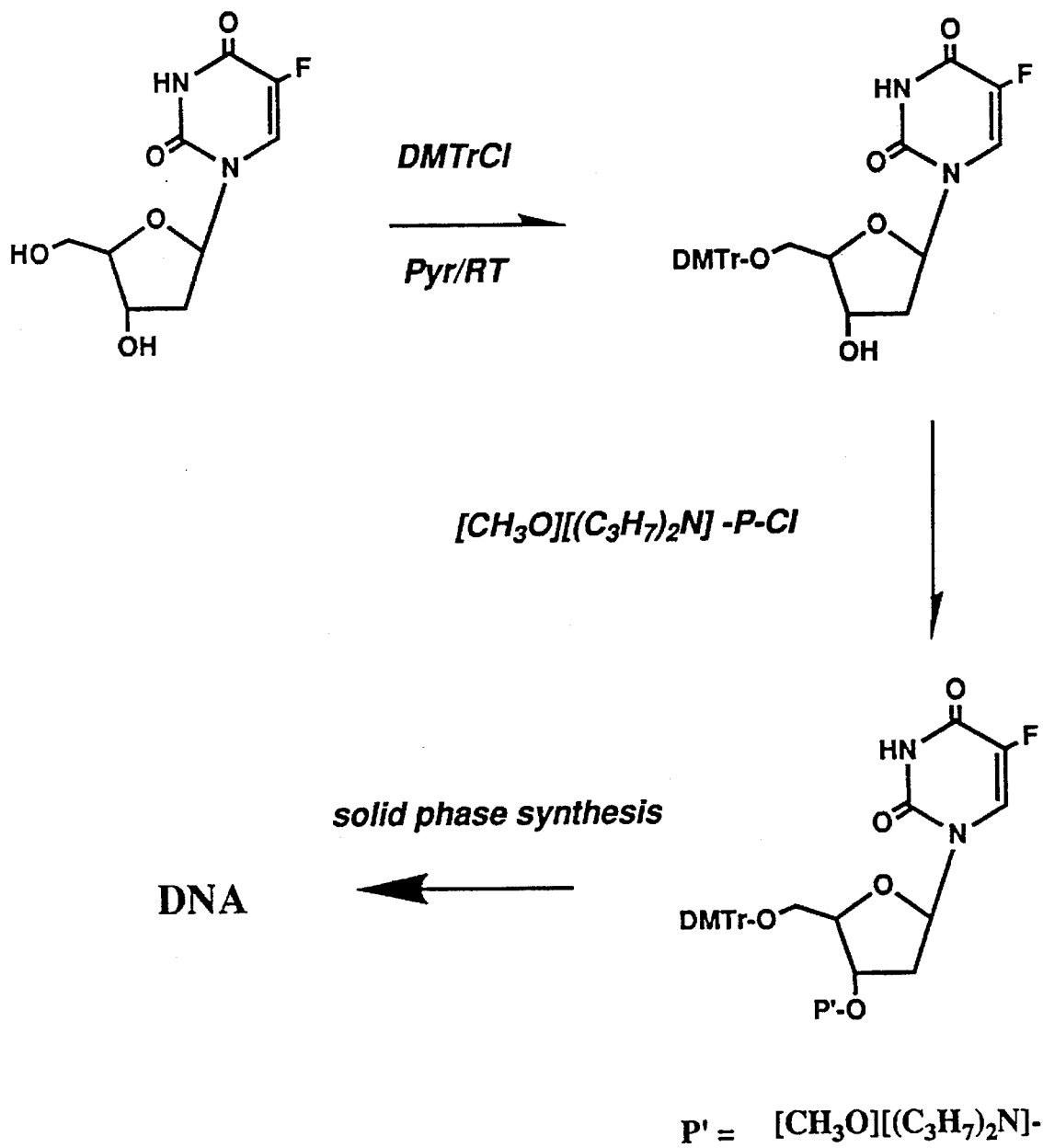
FIG. 3 is a diagrammatic illustration showing a preferred method of preparing homo-oligomeric 5-fluorodeoxyuridine-5'-O-monophosphate.
Figure 4:
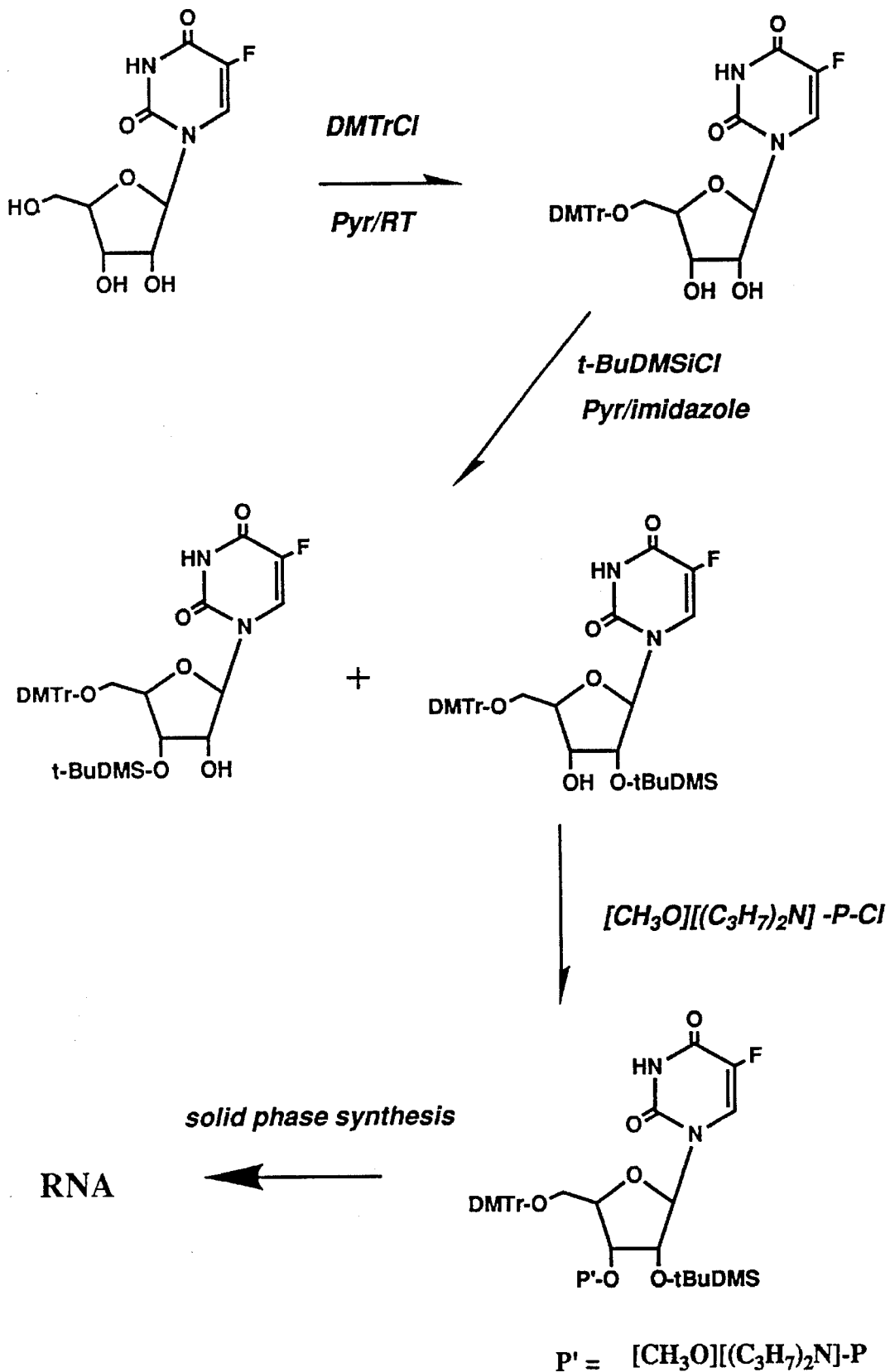
FIG. 4 is a diagrammatic illustration showing a preferred method of preparing homo-oligomeric 5-fluorouridine-5'-O-monophosphate.

FdU$_n$ and FrU$_n$ synthesis is preferably performed on an Applied Biosystems 380B DNA synthesizer. The synthesis conditions are essentially the same as the standard 10 µmole cycle, but utilizes the 5'-O-[4,4'-dimethoxytrityl]-[ 3'-O-diisopropylcyanoethyl-phosphonamidic-chloride]-[2'-O-t-butyl-dimethylsilyl]- 5-fluorouridine for FrU$_n$ preparation, (or 5'-O-[4,4'-dimethoxytrityl]-[ 3'-O-diisopropylcyanoethyl-phosphonamidic-chloride]-5-fluorodeoxyuridine for FdU$_n$ preparation) as the sole nucleoside phosphoramidites in each coupling cycle. The number of coupling cycles may be varied from two to any number with the most useful number of cycles being eight to 24. After synthesis, the FdU$_n$ is cleaved from the CPG support by treatment with 28% ammonium hydroxide (90 min, room temperature). For FrU$_n$, the ammonium solution is then heated in a sealed tube at 55° C. overnight to remove the protecting groups. The crude material is then desalted on Sephadex G-25 prior to purification by HPLC. The solution is decanted off and the CPG is washed with anhydrous methanol. The completely deprotected material is then purified by HPLC. Aliquots of 200–250 ODU are purified on a Protein-Pak DEAE-5PW anion exchange column (22.5 mmx 150 mm). A gradient from 0–0.15M sodium perchlorate (90 min) at 5 ml/min is used to elute the product. Pure fractions are combined, lyophilized, and desalted on Sephadex G-25. All FdU$_n$ and FrU$_n$ is handled with gloves and sterile water and consumables are used at all times. (FIGS. 3 & 4).

III. Enhanced Methods of Delivery

A. Timing Production of Cytotoxic Metabolite(s) to Cell Cycle Susceptibility

Mammalian cells internalize oligonucleotides and their derivatives by an endocytotic mechanism (see review Vlassov and Yakubov, 1991 and Crooke, 1993). It is clear that oligonucleotide derivatives can affect functions of specific nucleic acids in vitro and inside cells (Degols et al., 1991; Hél`ene and Toulmé, 1990; Cohen, 1989). Incubation of cells with radio-labeled oligonucleotides results in binding of the radioactive material to the cells and its accumulation in the cell nuclei (Vlassov et al., 1986 and Zamecnick et al., 1986). Uptake is relatively rapid as cells exposed to a 20-mer at a concentration of 20 μM produced a cellular concentration of 1.5 μM within 15 minutes (Goodchild et al., 1988). Autoradiography of cells reveals label in both cytoplasm and nucleus of the cells (Iversen et al., 1993). Further, oligonucleotides with an alkylating group, an aromatic nitrogen mustard at the 5' terminal phosphate provide direct evidence of the intracellular localization (Karpova et al., 1980 and Vlassov et al., 1986b).

Detailed studies on the mechanism of cell uptake have been performed with fluorescently labelled oligonucleotides. Oligonucleotides are taken up by cells in a saturable manner compatible with endocytosis. Maximal binding is achieved within 2 hours of incubation. The process is slowed by decreased temperature and inhibitors of endocytosis such as deoxyglucose, cytochalasin B and sodium azide. Further 20% of the material was taken into nuclei and 50% was associated with mitochondria, lysosomes and other vesicular structures (Loke et al., 1989; Neckers, 1989; and Iversen et al., 1993). Once in the cytoplasm but not in vessicles the oligonucleotide is rapidly transported to the nucleus (Chin et al., 1990 and Leonetti et al., 1991). Different cell lines bind different amounts of oligonucleotides. The efficiency of oligonucleotide internalization depends on the conditions of cell growth. An increase in the cell monolayer density from $8\times10^4$ to $5\times10^5$ cells/cm$^2$ resulted in a 3-fold decrease in maximal binding of the oligomer per cell (Ceruzzi and Draper, 1989).

Since oligonucleotide binding is saturable, a receptor at the cell surface capable of mediating cellular uptake is suggested. The binding is trypsin sensitive indicating the transport involves a protein (Emlen et al., 1988). An oligonucleotide with an N-hydroxy-succinimidyl (NHS) ester attached to the "Denny-Jaffe" cross-linking reagent and an oligonucleotide with an aminolinker group at the 5' end is incubated in cells in the dark. Then cells are exposed to ultraviolet light which activates the cross-linking reagent to associated proteins revealing an 80-kDa protein, the putative receptor (Neckers, 1993 and Geselowitz and Neckers, 1992). DNA binding is most likely mediated by this receptor in platelets, leukocytes and lymphocytes (Dorsch, 1981; Ohlbaum et al., 1979; Bennett et al., 1985; and Diamantstein and Blitstein-Willinger 1978). Finally, this receptor is linked to cellular functions and pathophysiology (Bennett et al., 1987 and Bennett et al., 1986).

Tumor cells are for the most part rapidly dividing. Many anti-tumor drugs, including 5-FU and its derivatives, are designed to inhibit DNA synthesis. FdUMP inhibits thymidylate synthase (TS) and results in a lack of dTTP which is one of the four nucleotides necessary for DNA replication and hence cell-division. The thymidineless state has not been definitively shown to be cytotoxic apart from its inhibition of DNA replication and cell division. Cells undergo DNA replication during S-phase of the cell cycle. Delivery of FdU$_n$ to cells at the onset of S-phase is thought to efficiently inhibit dTTP production and shutdown DNA replication and cell division. Cells prepared to undergo DNA-replication and inhibited from doing so then presumably self-destruct (or are exceedingly vulnerable to external cytotoxic agents such as free radicals). Some tumor cells may be dividing only slowly and delivery of FdU$_n$ at an inopportune point in the cell cycle may not have the desired cytotoxic effect. Whatever TS is expressed is inhibited but the FdUMP produced eventually degrades with little impact on the ability of the cell to replicate DNA or undergo cell division. Slowly dividing cells require sustained release of FdUMP so that it is present in sufficient quantities whenever DNA synthesis proceeds. Conjugation of FdU$_n$ at the 3' or 5' terminal hydroxyl with a bulky substituent may slow exonuclease action and result in steady state levels of FdUMP that are inhibitory of DNA replication over a prolonged time. Alternatively, delivery of FrU$_n$ results in FUMP being released by exonuclease action. FUMP is readily metabolized to FUTP and incorporated into all species of RNA. Natural degradation of RNA releases FUMP that may be converted to FUDP and reduced to FdUDP by ribonucleotide reductase and converted to FdUMP. This process results in steady-state levels of FdUMP that inhibit DNA replication and cell division. Delivery of FdU$_n$ and FrU$_n$ simultaneously is also an effective way in which to prevent tumor cells from undergoing DNA replication and cell division whether they are just entering S-phase and beginning DNA replication or are in other phases of the cell cycle where immediate high levels of FdUMP have little effect.

B. Methods of Producing Target Specific Delivery

Transformed cells that constitute a solid tumor are known to express characteristic antigenic components on their cellular surface. This observation is the basis for radio-immunoconjuage therapy in which radio-labelled monoclonal antibodies specific for tumor cell antigens are used to deliver a toxic dose of radioactivity directly to tumor cells. Similarly, conjugation of homo-oligomeric FdUMP via a labile linker with an antibody fragment directs the homo-oligomeric FdUMP to tumor cells. Cleavage of the labile linker releases homo-oligomeric FdUMP in high concentrations in the vicinity of the tumor and in low concentrations elsewhere. This improves the therapeutic index for the drug by lowering the dose needed to be cytotoxic to tumors because it is present in higher concentrations locally near the tumor. Release of cytotoxic metabolites (FBAL) is thus decreased.

C. Methods of Increasing Cellular Uptake

The delivery of 5-fluorodeoxyuridine 5'-O monophosphate (FdUMP) as homo-oligomeric 5-fluorouridine leads to increased cellular uptake. Other homo-oligomeric anti-metabolites nucleotides also have increased cellular uptake. It is known that the nucleoside base 5-fluoruracil (5-FU) easily penetrates the cellular membrane and that the nucleosides 5-fluorodeoxyuridine (FdU) and 5-fluorouridine (FrU) also gain entry to the cell. The mononucleotide FdUMP, the species responsible for thymidylate synthase (TS) inhibition, does not appreciably penetrate the cellular membrane. Data with $FdU_n$ with both phosphorothioate and phosphodiester backbones strongly suggests that these homo-oligomers efficiently gain entry to the cell. The efficiency of cellular uptake is underscored by the increased effectiveness as cytotoxic agents of $FdU_n$ per residue of FdU relative to monomeric $FdU_n$. The increased cellular uptake is a function of the oligomeric nature of these compounds. Entry of one $FdU_n$ releases n residues of FdUMP. The increased effectiveness of homo-oligomeric FdUMP relative to monomeric nucleosides or nucleoside bases is also a function of the natural degradation processes in the cell that degrade the oligonucleotide via 3' exonuclease action to release FdUMP (the potent inhibitor of TS). Direct production of FdUMP circumvents the steps of metabolism required for production of FdUMP from 5-FU, FrU, or FdU. FdUMP in monomeric form does not appreciably penetrate the cellular membrane. This is also an important distinction between homo-oligomeric FdUMP and oligomers or polymers that are based on ethylene glycol or oligosaccharide polymeric backbones. Such organic based polymers do not penetrate the cellular membrane intact because they do not interact with the cellular membrane in the same way as do oligonucleotides with either a phosphodiester or phosphorothioate backbone. Further, even if they were taken up intact by a cell, their chemical or enzymatic degradation would not directly yield FdUMP, but a precursor to FdUMP that must be enzymatically activated.

Cellular uptake of $FdU_n$ and $FrU_n$ is enhanced by conjugation at either the 3' or the 5' terminal hydroxyl with lipophilic moities such as cholesterol or cationic amino acids such as L-lysine or poly-L-lysine. Such derivitization has proven useful in studies with other oligonucleotides in improving cellular uptake above the relatively good uptake of the native oligonucleotides. Such conjugation increases the affinity of the oligonucleotides for the cellular membrane or reduces electrostatic repulsions for the oligonucleotide while in the hydrophobic membrane or possibly promotes cellular uptake via receptors that recognize the conjugated species.

The presence of lipophilic or cationic moieties at the termini effects subcellular distribution and metabolism. In particular, 3'-terminus derivatization hinders 3'-exonuclease activity and retards the enzymatic degradation of $FdU_n$ and $FrU_n$. Preferably a preparation of $FdU_n$ or $FrU_n$ with cholesterol, ethyl-spaced adamantane, and 1,2-di-hexadecyl glycerol at either the 5' or the 3' termini are utilized.

It is preferred that a preparation of 5'-derivatized $FdU_n$ or $FrU_n$ is made by reaction of the 5'-hydroxyl of the oligomeric compound while still attached to controlled pore glass beads with a reactive hydrophobic or lipophilic phosphoramidite. The preparation of the reactive phosphoramidites of cholesterol, an ethyl-spaced adamantane, and 1,2-di-hexadecyl glycerol is shown in FIG. 7.

The dry alcohols are dissolved in anhydrous dichloromethane and reacted with 2-cyanoethyl-N,N-diisopropylphosphoramidochloridite by using diisopropylethylamine as a base. The reaction proceeds under an Argon atmosphere and is quenched with ethyl acetate and purified by flash chromatography on silica gel. The phosphoramidites are then used in an ABI solid-phase DNA synthesizer. Preferably a normal coupling cycle is utilized (this may be modified so as to improve coupling efficiency). The oligonucleotides are then removed from the CPG support and purified as described herein before.

Figure 6:
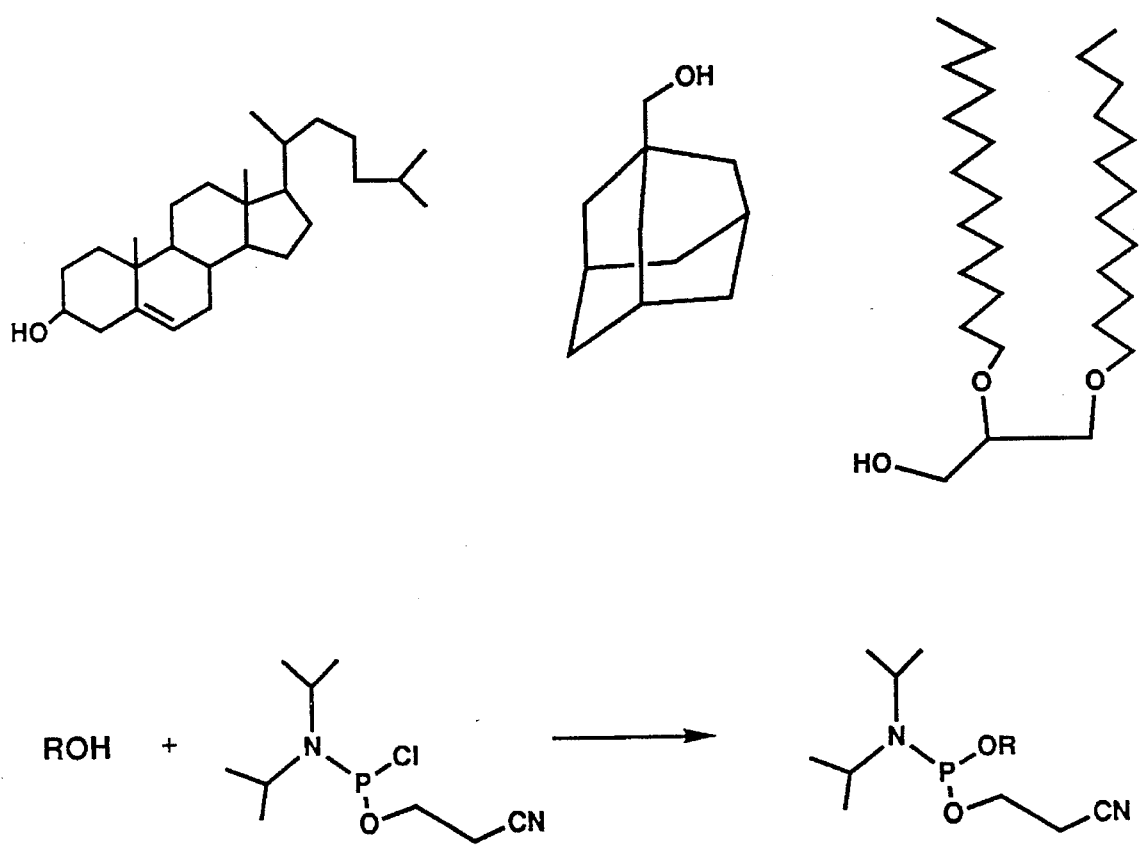
FIG. 6 is a diagrammatic illustration showing a preferred method of preparation of the reactive phosphoramidites of cholesterol, an ethyl-spaced adamantane, and 1,2-di-hexadecyl glycerol at the 5' termini.
Figure 7:
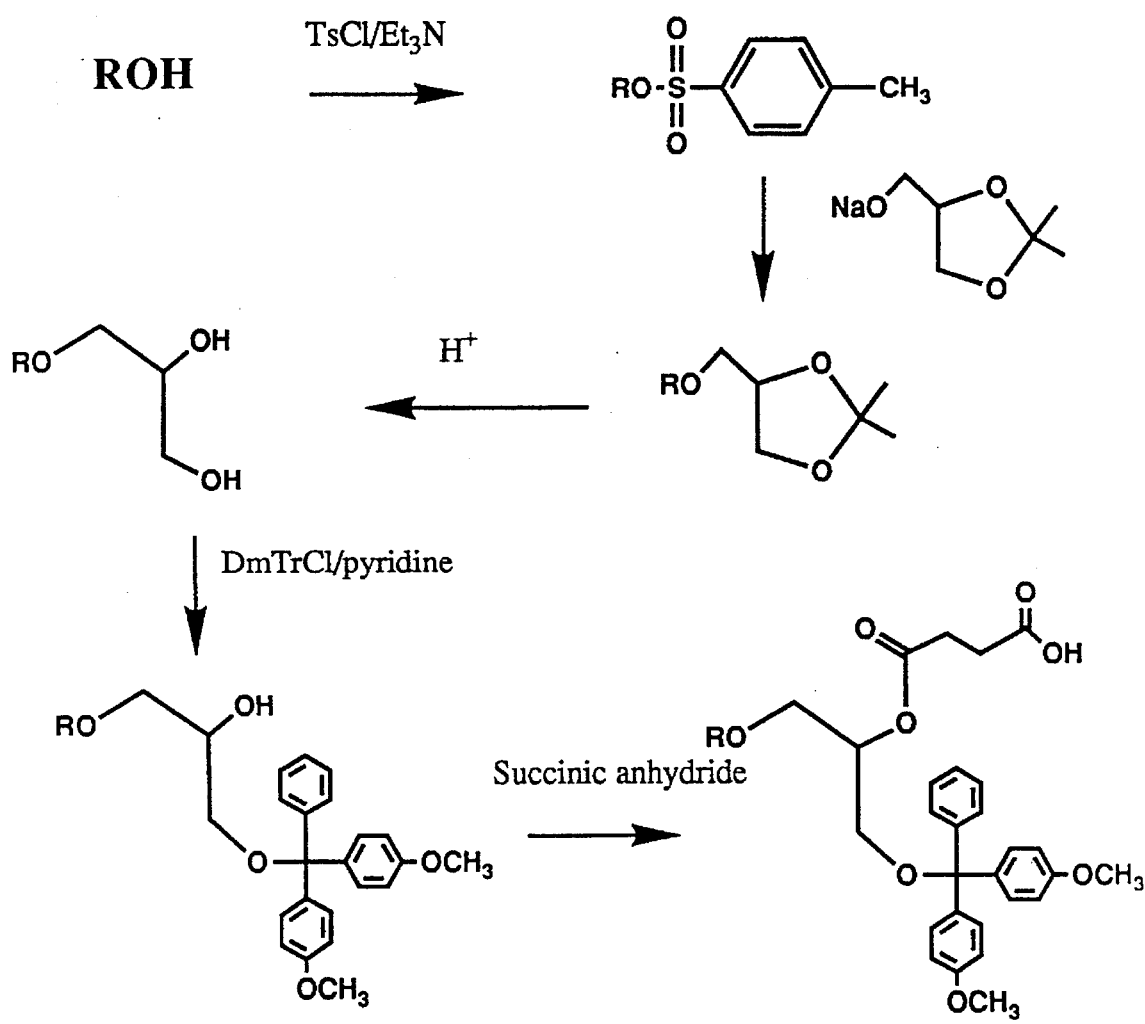
FIG. 7 is a diagrammatic illustration showing a preferred method of preparation of the reactive phosphoramidites of cholesterol, an ethyl-spaced adamantane, and 1,2-di-hexadecyl glycerol at the 3' termini.

The attachment of lipophilic moieties to the 3' terminus may be accomplished as depicted in FIG. 7. The same alcohols shown in FIG. 6, cholesterol, ethyl-spaced adamantane, and 1,2-di-hexadecyl glycerol are first tosylated. The tosyl group is then displaced by the sodium salt of solketal. The acetonide is then deprotected with mild acid. The primary alcohol is then dimethoxytritylated and the secondary alcohol reacted with succinic anhydride to form the succinates. These are then reacted with long-chain alkylamine controlled pore glass in the presence of catalytic amounts of dimethylaminopyridine and stochiometric amounts of 1-(3-dimethylaminopropyl)-ethylcarbodiimide in anhydrous pyridine. The loading capacity of the derivatized CPG is determined by trityl analysis at 600 nm following exposure to acid. The derivatized support is then suspended in a mixture of acetic anhydride (5 mL), 2,4,6 collidine (7 mL), and DMAP (3 g) in anhydrous THF (100 mL) and shaken for two hours. The CPG is then washed with dichloromethane and loaded at the appropriate capacity, e.g., 1 or 10 μmole, into columns for use in an ABI solid-phase DNA synthesizer.

IV. Biological Evaluation of $FdU_n$ and $FrU_n$ and their Conjugates

A variety of pro-drug forms of 5-FU have been developed to address the issues of cellular uptake, sustained release, organ distribution, and transdermal or intestinal uptake that are problematic for the native drug. One of the most widely studied pro-drug forms of 5-FU is 5'-deoxy-5-fluorouridine (DFUR). DFUR is converted to 5-FU by pyrimidine nucleoside phosphorylase but has better cellular uptake properties than 5-FU. Like 5-FU, DFUR also releases FBAL as a toxic metabolite. Other nucleoside analogues of FUr include Tegafur [(1-(2-tetrahydrofuryl)-5-fluoruracil], Ftorafur [R, S-1-(tetrahydro-2-furanyl)- 5-fluorouracil] and a variety of 5-fluorocytidine derivatives.

A variety of polymeric forms of 5-fluorouridine have also been prepared to provide sustained release of 5-FU. 5-Fluorouracil has been prepared as both conjugates of chitooligosaccharides and poly(ethylene glycol). These polymeric forms were designed to provide macromolecular drugs with reduced side-effects and strong anti-tumor activity and showed good biological activity and low toxicity in animal models. The chief advantages of $FdU_n$ and $FrU_n$ compared to other polymeric structures are that the oligonucleotide based oligomers are readily taken up by cells (most likely through a facilitated mechanism ). Also, enzymatic degradation of the oligomeric 5-fluorodeoxyuridine results directly in release of the fully activated inhibitor of thymidylate synthase (FdUMP). Oligonucleotide based polymers retain the advantages that make other polymers useful (e.g., increased bioavailability).

Data demonstrates that oligomeric 5-fluorodeoxyuridine is more potent than monomeric 5-fluorouridine. Rat hepatocytes, H4IIE cells, were plated at a density of $1 \times 10^4$ cells per well in a 96 well microtiter plate and allowed 18 hours to become adherent. The cells were bathed in RPMI 1640 culture medium with 10% fetal calf serum containing $FdU_n$ compounds or monomeric 5-fluorodeoxyuridine at concentrations of 0, 0.01, 0.03, 0.1, 0.3, 1.0, 3.0, and 10 μM. After 48 h, MTT (3-(4,5-dimethylthizoyl-2-yl)-2,5-diphenyl tetrazolium bromide) was added and the resulting insoluble formazon production was monitored spectrophotometrically at 540 nm. Cell viability was calculated from the amount of formazon produced. Studies with oligomers of length 8, 12, and 16 (with both normal phosphodiester and thiophosphate backbones) have demonstrated the following:

TABLE I

Effects of length and backbone on cytoxicity of oligomeric 5-fluorouridine

| Length n = | P(O) $LD_{50}$ FdU/FdU-N[1] | Relative Potency[2] | P(S) $LD_{50}$ FdU/FdU-N | Relative Potency |
|---|---|---|---|---|
| 8 | 14.7 | 1.8 | 1.8 | 0.22 |
| 12 | 28.9 | 2.4 | 2.7 | 0.22 |
| 16 | 51.6 | 3.2 | 3.4 | 0.21 |

[1]The ratio of the estimated lethal dose to 50 percent of the cells in culture for fluorouridine monomer over fluorouridine polymer of length N, are defined in the left column. P(O) = phosphodiester backbone and P(S) = phosphorothioate backbone.
[2]The relative potency is established as the ratio of $LD_{50}$s divided by the number of fluorouridine residues to the polymer. This provides the potency per residue of fluorouridine for direct comparison.

[1]The ratio of the estimated lethal dose to 50 percent of the cells in culture for fluorouridine monomer over fluorouridine polymer of length N, are defined in the left column. P(O)= phosphodiester backbone and P(S)= phosphorothioate backbone.

[2]The relative potency is established as the ratio of $LD_{50}$s divided by the number of fluorouridine residues to the polymer. This provides the potency per residue of fluorouridine for direct comparison. Thus:

the cytotoxic potency produced by oligomeric 5-fluorouridine is greater per residue than that produced by monomeric 5-fluorouridine;

the hydrolysis of the backbone to liberate FdUMP is essential as the nuclease resistant phosphorothioate backbone demonstrates diminished potency relative to the phosphodiester; and increasing the length of the phosphodiester homo-oligomeric nucleotide produces increased potency per residue of 5-fluorouridine.

The data suggest oligonucleotide transport across cell membranes, and/or circumvention of enzymatic steps required for conversion to FdUMP, increase the potency of the oligomeric compounds relative to monomeric nucleosides.

The present inventors have also studied the cellular binding and transport of oligomeric 5-fluorouridine across cell membranes. These studies provide evidence of a cellular transport system for oligonucleotides that does not transport mononucleotides. Nekkers has shown that antisense oligonucleotides are taken up intact by cells in a length-dependent and charge-dependent manner. Mutant cell (which have lost some features of oligonucleotide transport) lines were derived from the rat liver hepatocyte, H4IIe cells, and are referred to as AMRC1.7 and AMRC1.12 cells. Preliminary data concerning these cells and the comparison of FdU and $FdU_8$ is shown in Table II. The data indicate that there is a cell-dependent uptake (or processing) phenomena that effects the relative potency of the oligomeric 5-fluorouridine. The oligomeric compound is more potent on a per residue basis than the mononucleoside in all cell lines except those deficient in oligonucleotide uptake. We have evaluated the cytotoxicity of dU and $dU_8$ using these same cells and assay methods and observed no toxicity up to 10 uM concentrations. Thus, contaminants from synthesis that might persist following purification are not potential explanations for the cytotoxicity observations. These data clearly demonstrate the differences between cell lines and the cytotoxic response to oligomeric 5-fluorodeoxyuridine. This provided the rationale for our evaluating multiple cell types for their response to a variety of oligomeric 5-fluorouridine compounds:

TABLE II

Comparison of FdU-8 with FdU cytotoxicity in reduction of a variety of cell lines

| Cell Type | $LD_{50}$ FdU/FdU-8 | Relative Potency |
|---|---|---|
| H4IIe - Rat Hepatocyte | 35.6 | 4.20 |
| AMRC1.7 | 7.1 | 0.89 |
| AMRC1.12 | 5.8 | 0.73 |
| 3T3 Mouse Fibroblast | 9.8 | 1.23 |
| 168 Metastatic mouse cell | 9.6 | 1.2 |
| 410 Highly Metastatic mouse cell | 10.7 | 1.34 |

Studies concerning the pharmacokinetics of oligonucleotides have also been conducted. Work has been completed in the mouse, rat, rabbit, monkey, and human and has involved a number of different oligonucleotides. While the pharmacokinetic behavior of an oligonucleotide cannot be predicted at this time, we have observed elimination half-life ranging from 7 to 57 hours for phosphorothioate oligonucleotides intravenously injected into mice. Hence, it seems reasonable to assume the pharmacokinetic behavior of oligomeric 5-fluorouridine will most likely involve a half-life of several hours. Since the half life of 5-FU is about 15 minutes in humans, the oligomeric 5-fluorouridine compounds are very likely to have a significantly longer residence time. This should result in a substantial reduction in the dose required to produce an equivalent plasma concentration. The reduction in total body burden combined with increased potency of 5-fluorouridine per residue indicates a potential improvement in treatment of cancers with reduced side effects. This suggests a substantial improvement in the therapeutic index of FdU anti-metabolite in the clinical management of cancer. Delivery of 5-fluorouridine in oligomeric form should result in drugs that are more selective, more powerful, and more bioavailable compared to their monomeric counterparts. Further, the advances made in combination chemotherapy involving 5-FU will still be useful with these oligomeric forms. In particular, leucovorin (folinic acid) is expected to potentiate $FdU_n$ by increasing 5,10-$CH_2$-tetrahydrofolate levels. This will result in a greater preponderance of stable ternary complexes involving FdUMP derived from $FdU_n$, TS and 5,10-$CH_2FAH_4$.

The methods described herein for 5-FU delivery as an anti-cancer agent may be generalized to other nucleoside analogues that are anti-cancer or anti-viral agents. Schmidt et al. have proposed incorporation of 5-fluoro-2'-deoxycytidine into oligodeoxynucleotides. They proposed that such selectively incorporated fluoropyrimidines could be used to study the mechanism of cytosine methyl transferases. However, the present specification is the first proposed synthesis of oligomeric compounds consisting solely of nucleosides that have anti-cancer activity or anti-viral activity as monomers.

A. Methods of Pharmacokinetic and Toxicological Analysis

Prior to undertaking animal studies on the efficacy of oligomeric 5-fluorouridine compounds for tumor reduction, a toxicology study using Sprague-Dawley rats is preferably conducted. (These animals are preferred in order that sufficient blood and urine samples may be collected for analysis). Three groups with five males and five females in each group are preferably studied. Group one receives a saline solution. Group two receives the functionalized oligomeric 5-fluorouridine compound with the apparent most promising cell-culture performance. Group two is sacrificed on day 8. Group three is treated as is group 2 but is sacrificed on day 28. The oligomeric 5-fluorouridine compounds are delivered at a dose of 1000 mg/m² by using a 7 day Alzet infusion pump implanted subcutaneously. Each rat is identified by a unique number on the tail with the numbers posted on the cage. Rats are fed a diet of Purina rodent chow 5240 and tap water. Body weight, food consumption, and water consumption is recorded daily. Blood samples of 0.5 mL are recovered from the catheter once per day during treatment and twice a week during the three week post infusion interval. Blood chemistry evaluation and urinalysis are also performed. Blood chemistry analysis preferably includes LDH, AST, alkaline phosphatase, blood urea nitrogen, plasma creatine concentration, bilirubin, glucose, albumin, and total protein. Blood analysis includes white cell count, red cell count, hemoglobin, and hematocrit. Radioactivity in blood is determined by liquid scintillation counting. Gel electrophoresis is preferably performed to determine the size distribution of the radioactive material. Blood chemistry is evaluated on days -1, 1, 3, 5, and 7 of the infusion and once per week during the three week post-infusion interval. The total urine volume is also measured daily. Analysis of urine for color, pH, radioactivity, and dipstick is preferably performed on each 24 hour urine sample. Gel electrophoresis is performed on samples to determine the size distribution of the radioactive material in the urine. If significant toxicity is observed at this dose an additional repeat of this study may be performed at 300 mg/m². If no toxicity is observed then a safe margin is indicated.

B. Methods for Determining the Biological Activity of $FdU_n$ and $FrU_n$ Compounds Against Tumors in a Mouse Model The potential clinical utility of a few of the oligomeric 5-fluorouridine compounds most promising in the cytotoxicity assays described before are preferably assessed via a mouse melanoma model. The B16-BL6 melanoma is available from the DCT Tumor Bank, National Cancer Institute, Frederick, Md. This is a highly invasive and metastatic subline of the B16 melanoma originally isolated by Fidlet. The tumor is preferably maintained in plastic tissue culture flasks in a humidified atmosphere containing 5% $CO_2$ in air. The culture medium used is minimal essential medium supplemented with 10% fetal calf serum, 2 mM glutamine, 0.1 mM non-essential amino acids, vitamins, a mixture of 100 U/mL penicillin and 100 μg/mL streptomycin and designated complete essential medium (CMEM). Each C57BL/6J mouse is given a subcutaneous injection of $5\times10^4$ viable tumor cells (0.1 mL) into the right flank. The subcutaneous tumors are measured with a vernier caliper. Measurements are calculated preferably as the geometric mean of two diameters, the first being the longest diameter and the second being measured perpendicular to the first diameter. Tumor growth is followed for 21 days. Four groups of 10 mice (5 male/5 female) are used for each compound. The first group receives saline solution while groups 2, 3, and 4 receive 50, 150, and 300 mg/m² of oligomeric 5-fluorouridine compounds delivered daily for seven days following the day after tumor inoculation. The oligomeric 5-fluorouridine compound is infused by using 14 day Alzet infusion pumps implanted subcutaneously. Mice are fed and cared for as in the rat toxicity study described before. Control experiments with 5-fluoruracil are also conducted simultaneously. Efficacy of the oligomeric 5-fluorouridine compounds are measured in their absolute success in inhibiting tumor growth and in their success relative to 5-FU at equivalent and lower doses.

The oligomeric 5-fluorouridine compounds tested against the mouse melanoma model are also preferably tested in mice against Lewis lung carcinoma. The Lewis lung carcinoma was obtained from the Division of Cancer Treatment Tumor Bank (National Cancer Institute), Frederick Cancer Research Facility (Frederick, Md.). The tumor is cultured in plastic tissue culture flasks in a humidified atmosphere of 5% $CO_2$ in air. The Lewis lung carcinoma cells are cultured on media consisting of Dulbecco's minimal essential medium and glutamine, supplemented with 10% fetal calf serum, 100 IU penicillin/mL, and 100 ug streptomycin/mL. Cells are harvested after treatment of the monolayers with a mixture of trypsin (0.5%) and EDTA (0.2%) for one minute. The single cells are washed in media and resuspended in phosphate buffered saline (PBS). Viable mammary carcinoma cells (5×104 in 0.2 mL of PBS) are injected into the tail vein of C57BL/6J mice. The same feeding, care, and drug administration protocols described for the mouse melanoma model are followed. The rate and growth of the primary tumors is measured with calipers. In addition, after three weeks the animals are sacrificed and the lungs are removed and fixed in buffered formalin for 24 h and the number of metastatic foci on the surface of the lung are counted with the aid of a dissecting microscope.

V. Utilization of $FdU_n$ and $FrU_n$ as a Chemotherapeutic Agents

Homo-oligomeric FdUMP and homo-oligomeric FUMP or their conjugates are to be used clinically as anti-cancer agents. Tumor targets are the solid-tumors of the breast, head, neck, colon and elsewhere that are currently targets for 5-FU chemotherapy. An intravenous blous administration is currently thought preferred (5-fluorouracil administration approved protocols are followed). Combination chemotherapy involving leucovorin and B-interferon is also expected to be effective with these homopolymers as for the nucleoside and nucleoside base. It is anticipated that therapeutically active doses of $FdU_n$ and $FrU_n$ will deliver less 5-fluoruracil because of their (1) greater bioavailability (due to longer residence time in-vivo); (2) efficiency of cellular uptake; and (3) natural degradation directly to the active metabolites. The lower doses (i.e. less 5-fluorouracil) produce lower levels of FBAL and are less neurotoxic and cardiotoxic, thus improving the therapeutic index of the drug relative to delivery as 5-fluorouracil.

It should be apparent to those skilled in the art that a non-homooligomer containing antimetabolites such as 5-FU interspersed in a sequence of other nucleotides or nucleotide analogues will provide similar advantages to the homo-oligomer. This would include oligonucleotides with sequences capable of modulating gene expression through antisense, antigen, or as binding sites for endogenous materials which are involved in the process of transcription. Finally, preparations of oligonucleotides capable of forming double, triple or quartet strands represent an extension of the fundamental advantages of a homo-oligomer.

VI. Conclusion

Thus, there has been described: (1) a method of synthesizing useful oligomeric species of 5-fluorouracil; (2) methods of utilizing oligomeric species of 5-fluorouracil in the treatment of solid tumors wherein bioavailibility is increased; (3) and methods of enhancing the delivery of oligomeric species of 5-fluorouracil such that (a) cytotoxic metabolite delivery is timed for optimum tumor cell lethality, (b) the cytoxic metabolites are tumor target specific, and (c) tumor cell uptake is optimized.

It will be apparent to those both skilled in the art, and familiar with the present disclosure, that many modifications and additions may be made to the present invention, for example, ( 1 ) other methods of synthesis may be utilized and the principles disclosed herein may be adapted for preparing oligomers of other chemotherapeutic agents; (2) other methods of utilizing oligomeric species of 5-fluorouracil for the treatment of diseases are anticipated wherein the general principles of the instant invention are utilized; (3) and other methods of enhancing the delivery of oligomeric compounds are also anticipated such that (a) drug delivery is timed for optimum pharmacokinetic effect, (b) target specific drugs are produced, and (c) adverse effects are minimized.

Thus, there has been described a method of increasing the efficacy of treatments utilizing 5-fluorouracil which accomplishes at least all of the stated objects, including disclosure teaching the modification of other bio-active nucleoside analogues.

We claim:

1. A homo-oligonucleotide consisting essentially of between 2 and 26 monomers of 5-fluorodeoxyuridine 5'-monophosphate (FdUMP) covalently linked via 3'- to 5'-phosphodiester linkages, where at the 3'- or 5'-terminus there is covalently linked a molecule selected from the group consisting of cholesterol, ethyl-spaced adamatane, 1,2-dihexadecylglycerol and poly-L-lysine.

2. The homo-oligonucleotide of claim 1 wherein said molecule is covalently linked only at the 3'-terminus.

3. The homo-oligonucleotide of claim 1 wherein said molecule is covalently linked only at the 5'-terminus.

4. A homo-oligonucleotide consisting essentially of between 2 and 26 monomers of 5-fluorouridine 5'-monophosphate (FUMP) covalently linked via 3'- to 5'-phosphodiester linkages, where at the 3'- or 5'-terminus there is covalently linked a molecule selected from the group consisting of cholesterol, ethyl-spaced adamatane, 1,2-dihexadecylglycerol and poly-L-lysine.

5. The homo-oligonucleotide of claim 4 wherein said molecule is covalently linked only at the 3'-terminus.

6. The homo-oligonucleotide of claim 4 wherein said molecule is covalently linked only at the 5'-terminus.

7. A homo-oligonucleotide consisting essentially of between 2 and 26 monomers of 5-fluorodeoxyuridine 5'-monophosphate (FdUMP) covalently linked via 3'- to 5'-phosphothioate linkages, where at the 3'- or 5'-terminus there is covalently linked a molecule selected from the group consisting of cholesterol, ethyl-spaced adamatane, 1,2-dihexadecylglycerol and poly-L-lysine.

8. The homo-oligonucleotide of claim 7 wherein said molecule is covalently linked only at the 3'-terminus.

9. The homo-oligonucleotide of claim 7 wherein said molecule is covalently linked only at the 5'-terminus.

10. A homo-oligonucleotide consisting essentially of between 2 and 26 monomers of 5-fluorouridine 5'-monophosphate (FUMP) covalently linked via 3'- to 5'-phosphothioate linkages, where at the 3'- or 5'-terminus there is covalently linked a molecule selected from the group consisting of cholesterol, ethyl-spaced adamatane, 1,2-dihexadecylglycerol and poly-L-lysine.

11. The homo-oligonucleotide of claim 10 wherein said molecule is covalently linked only at the 3'-terminus.

12. The homo-oligonucleotide of claim 10 wherein said molecule is covalently linked only at the 5'-terminus.

* * * * *